(12) United States Patent
Bacher et al.

(10) Patent No.: US 12,011,393 B2
(45) Date of Patent: Jun. 18, 2024

(54) OCCLUSION SENSING IN OPHTHALMIC LASER PROBES

(71) Applicant: Alcon Inc., Fribourg (CH)

(72) Inventors: Gerald David Bacher, Carlsbad, CA (US); Nikki Koe, Irvine, CA (US); Bruno Lassalas, Foothill Ranch, CA (US); Alireza Mirsepassi, Irvine, CA (US); Dean Richardson, Aliso Viejo, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/647,660

(22) Filed: Jan. 11, 2022

(65) Prior Publication Data

US 2022/0125640 A1 Apr. 28, 2022

Related U.S. Application Data

(63) Continuation of application No. 16/593,138, filed on Oct. 4, 2019, now abandoned.
(Continued)

(51) Int. Cl.
*A61F 9/008* (2006.01)
*A61B 18/22* (2006.01)
*G02B 27/10* (2006.01)

(52) U.S. Cl.
CPC .......... *A61F 9/00821* (2013.01); *A61B 18/22* (2013.01); *G02B 27/10* (2013.01);
(Continued)

(58) Field of Classification Search
CPC ....... A61F 9/00821; A61F 2009/00863; A61B 18/22; A61B 2018/2266;
(Continued)

(56) References Cited

U.S. PATENT DOCUMENTS

2003/0234933 A1\* 12/2003 Nicolaides ......... G01N 21/1717
356/432
2004/0039378 A1\* 2/2004 Lin .................... A61B 18/20
606/6
(Continued)

FOREIGN PATENT DOCUMENTS

JP 2002-291764 A 10/2002
JP 2016-010809 A 1/2016
WO WO-2019017975 A1 \* 1/2019 ......... A61F 9/00808

OTHER PUBLICATIONS

Chinese Office Action dated Feb. 3, 2023, for Chinese Patent Application No. 201980064965.8.

*Primary Examiner* — Joseph M Dietrich
*Assistant Examiner* — Michael T. Holtzclaw
(74) *Attorney, Agent, or Firm* — PATTERSON + SHERIDAN, LLP

(57) ABSTRACT

In certain embodiments, a system for sensing occlusions in an optical system includes a first laser source configured to generate optical signals and a set of optical elements arranged to receive the optical signals from the first laser source and to direct the optical signals along a beam path. The system also includes a detector arranged to receive reflections of the optical signals traveling along at least a portion of the beam path and a control system communicably coupled to the detector. The control system is configured to detect, based on signals generated by the detector, reflection signals associated with the reflections of the optical signals, and disable a second laser source based on detection of the reflection signals.

10 Claims, 4 Drawing Sheets

Related U.S. Application Data

(60) Provisional application No. 62/742,075, filed on Oct. 5, 2018.

(52) U.S. Cl.
CPC .............. *A61B 2018/2266* (2013.01); *A61F 2009/00863* (2013.01)

(58) Field of Classification Search
CPC ........... A61B 2017/00123; A61B 2018/00636; A61B 2018/00785; A61B 2018/00898; G02B 27/10
USPC ............................................................ 606/4
See application file for complete search history.

(56) References Cited

U.S. PATENT DOCUMENTS

| | | | | |
|---|---|---|---|---|
| 2008/0285017 A1* | 11/2008 | Mitchell | ................ | A61B 18/22 |
| | | | | 356/73.1 |
| 2016/0334282 A1 | 11/2016 | Kallendrusch et al. | | |
| 2017/0290629 A1 | 10/2017 | Brown | | |
| 2019/0091067 A1* | 3/2019 | Kraemer | ............. | A61F 9/00834 |
| 2020/0163798 A1* | 5/2020 | Ban | ..................... | A61F 9/00808 |

* cited by examiner

OCCLUSION SENSING IN OPHTHALMIC LASER PROBES

PRIORITY CLAIM

This application:
(a) is a continuation of U.S. Non-Provisional patent application Ser. No. 16/593,138, titled "OCCLUSION SENSING IN OPHTHALMIC LASER PROBES," filed Oct. 4, 2019, whose inventors are Gerald David Bacher, Ronald T. Smith, Alireza Mirsepassi, Bruno Lassalas, Nikki Koe, and Dean Richardson, which is hereby incorporated by reference in its entirety as though fully and completely set forth herein, and
(b) claims the benefit of priority of U.S. Provisional Patent Application Ser. No. 62/742,075, titled "OCCLUSION SENSING IN OPHTHALMIC LASER PROBES," filed on Oct. 5, 2018, whose inventors are Gerald David Bacher, Ronald T. Smith, Alireza Mirsepassi, Bruno Lassalas, Nikki Koe, and Dean Richardson (U.S. Non-Provisional patent application Ser. No. 16/593,138 claimed the benefit of priority to U.S. Provisional Patent Application Ser. No. 62/742,075), which is hereby incorporated by reference in its entirety as though fully and completely set forth herein.

FIELD

The present disclosure relates to occlusion sensing in laser probes, such as laser probes useful in ophthalmic surgical procedures (e.g., multi-spot ophthalmic laser probes).

BACKGROUND

Laser probes may be useful in certain ophthalmic surgical procedures, such as laser photocoagulation therapy. Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach and eventually cause blindness.

In laser photocoagulation therapy, a laser probe, such as a multi-spot laser probe, is used to burn spots across the retina. In some cases, bleeding may occur during therapy, causing an occlusion near the tip of the laser probe. In some cases, other types of contaminants may be located near the probe tip, causing an occlusion near the probe tip. Such occlusions may lead to significant laser absorption at the tip, heating the probe tip and causing thermal-induced failure of the probe or injury to the patient.

SUMMARY

In certain embodiments, a system for sensing occlusions in an optical system may include a first laser source configured to generate optical signals and a set of optical elements arranged to receive the optical signals from the first laser source and to direct the optical signals along a beam path. The system may also include a detector arranged to receive reflections of the optical signals traveling along at least a portion of the beam path and a control system communicably coupled to the detector. The control system may be configured to detect, based on signals generated by the detector, reflection signals associated with the reflections of the optical signals, and disable a second laser source based on detection of the reflection signals.

In certain embodiments, an ophthalmic surgical system may include a connector configured to couple to a surgical probe that includes one or more optical elements, a treatment laser source; a probe laser source, a detector, and a set of optical elements. The optical elements may be configured to receive a treatment optical signal from the treatment laser source and direct the treatment optical signal along a first beam path toward the optical elements of the surgical probe, receive a probe optical signal from the probe laser source and direct the probe optical signal along a second beam path toward the optical elements of the surgical probe, and receive reflections of the probe optical signals caused by one or more of the optical elements in the surgical probe and direct the reflections of the probe optical signals toward the detector. The system may also include a control system communicably coupled to the detector. The control system may be configured to detect, based on signals generated by the detector, reflection signals associated with the reflections of the probe optical signals and disable the treatment laser source based on detection of the reflection signals.

In certain embodiments, a method for sensing occlusions in an optical system may include causing generation of first optical signals by a first laser source, causing generation of second optical signals by a second laser source, receiving, from a detector, signals based on optical signals received at the detector, detecting, based on the signals received from the detector, reflection signals associated with the reflections of the second optical signals, and disabling the first laser source in response to detecting the reflection signals.

In some embodiments, a function generator may generate modulation signals to modulate the optical signals used to detect occlusions (e.g., by modulating the probe laser signals). In some embodiments, a lock-in amplifier may be used to extract reflection signals based on the modulation signal generated by the function generator.

Certain embodiments may provide one or more advantages, in some instances. For example, certain embodiments may allow for sensing the presence or absence of blood or other contaminants on laser probe tips. When blood or other contaminants that could lead to probe failure or patient injury are sensed, a high-power treatment laser may be disabled to avoid any such issues. Detection of occlusions may be achieved prior to overheating of the laser probe, whereas previous techniques for detecting occlusions, such as blackbody-based techniques, may not detect occlusions until overheating has occurred.

These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
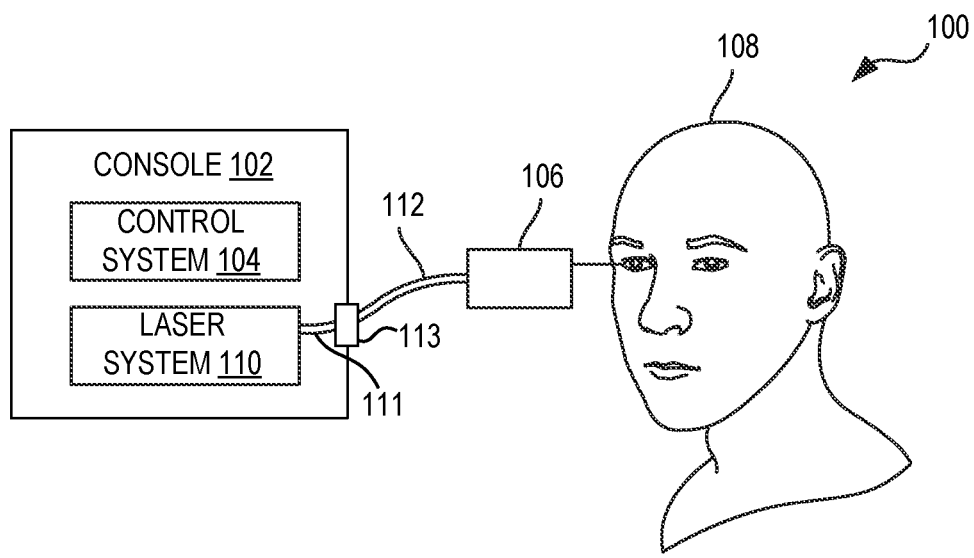
FIG. 1 is a diagram of an example ophthalmic surgical system that includes a laser probe.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

FIG. 1 is a diagram of an example ophthalmic surgical system 100 that includes a laser probe 106. The example system 100 includes a console 102 with a control system 104 and a laser system 110. In the example shown, the laser system 110 is in optical communication with the laser probe 106 through optical fibers 111, 112. The optical fiber 112 may attach to the console via connector 113. The connector 113 may include one or more optical elements for optically aligning the optical fibers 111, 112. The laser system 110 and laser probe 106 may be in optical communication via other techniques or implementations.

In some implementations, the example laser probe 106 is used by an operator (e.g., a surgeon) during a surgical procedure relating to the eye. For example, the laser probe 106 may be used in a laser photocoagulation therapy procedure for the eye of the patient 108, wherein the laser probe 106 is used to burn spots in the retina of the eye using a high-power treatment laser. A distal end of the laser probe 106 may be inserted into the eye of a patient 108 during such a procedure, as shown in FIG. 1.

In some cases, blood or other substances may cause an occlusion near the tip of the laser probe, leading to significant energy absorption at the tip of the laser probe 106 (i.e., the distal end of the laser probe 106), heating the probe tip and potentially causing thermal-induced failure of the probe or injury to the patient 108. Thus, in some embodiments, the laser system 110 may include a system for sensing such occlusions using a relatively low-power probe laser. In some cases, for example, the laser system 110 may include one or more of the components shown in FIG. 4 and described further below.

The example control system 104 that provides signals to one or more components of the laser system 110 to control operation of the laser system 110 or to perform other functions or operations as described herein. The control system 104 may include a processor, a memory, software, and firmware that are configured to perform such functions and operations. For example, in some embodiments, the control system 104 is implemented similar to the control system 424 of FIG. 4, as described further below.

The example laser system 110 generates optical signals for performing aspects of a surgical procedure on the eye of the patient 108. For example, the laser system 110 may include a femtosecond laser oscillator, such as a Ytterbium-based (e.g., a Yb:Glass or Yb-doped fiber) laser, an Erbium-based (e.g., an Er-doped fiber) laser, a Titanium Sapphire (TiAl2O3) laser, Chromium-based (e.g., Cr:LiSAF Cr:LiCAF, or Cr:LiSGAF) laser, an Alexandrite laser, a neodymium-doped yttrium aluminum garnet (Nd:YAG) laser, a semiconductor- or dye-based laser, or another type of laser for use in the surgical procedure. In some embodiments, the laser system 110 may include one or more of the components shown in FIG. 4 and described below.

Figure 2:
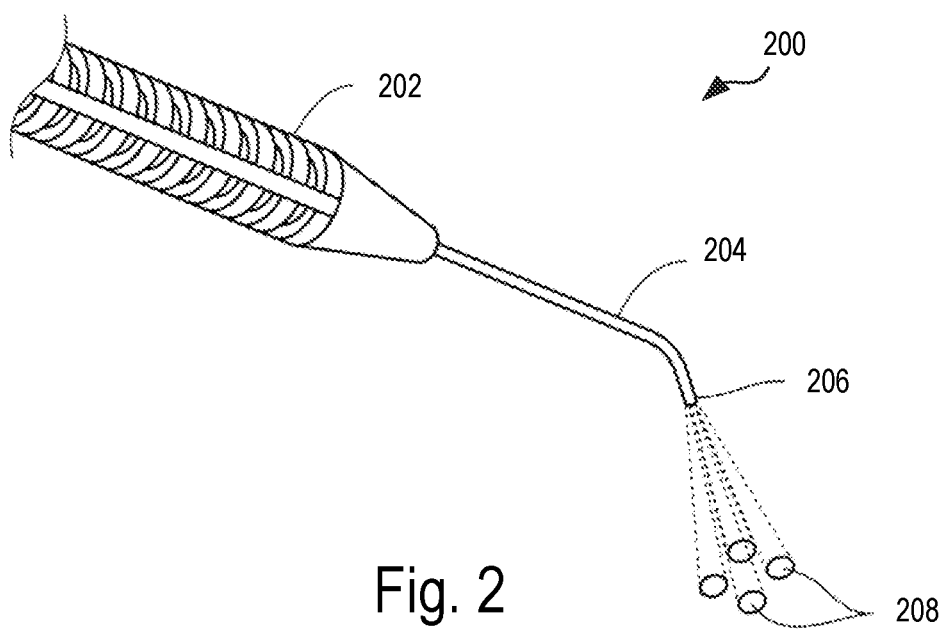
FIG. 2 is a diagram of an example of a multi-spot laser probe for use with an ophthalmic surgical system.

FIG. 2 is a diagram of an example of a multi-spot laser probe 200 for use with an ophthalmic surgical system (e.g., the ophthalmic surgical system 100 of FIG. 1). In the example shown, the multi-spot laser probe 200 generates four laser spots 208 simultaneously. Probe 200 comprises a handle 202 sized and shaped for grasping by a user, such as an ophthalmic surgeon. Probe 200 further includes a cannula 204 extending from handle 202 and having a tip 206 at a distal end (which may or may not be curved as shown in various embodiments). Cannula 204 is adapted for insertion into a patient's eye and may be cylindrically shaped. In various examples, cannula 204 may be made of stainless steel, titanium, nickel, nickel titanium (Nitinol), or platinum-iridium, and may be 23 Gauge, 25 Gauge, or 27 Gauge.

In operation, one or more laser beams from a laser source (e.g., a laser within the laser system 110 of FIG. 1) are transmitted through one or more optical fibers within handle 202 and cannula 204 and delivered from the distal tip 206 onto a retina, producing spots 208. In some examples, probe 200 comprises multiple fibers or a multi-core fiber, each transmitting a laser beam which produces a separate one of spots 208. In other examples, a single fiber may transmit a laser beam which is split (e.g., using a spherical lens or gradient-index (GRIN) lens in probe 200) to produce each one of spots 208. Various multi-spot laser probe designs are described in U.S. Pat. No. 8,951,244, which is incorporated by reference herein in its entirety.

Figure 3:
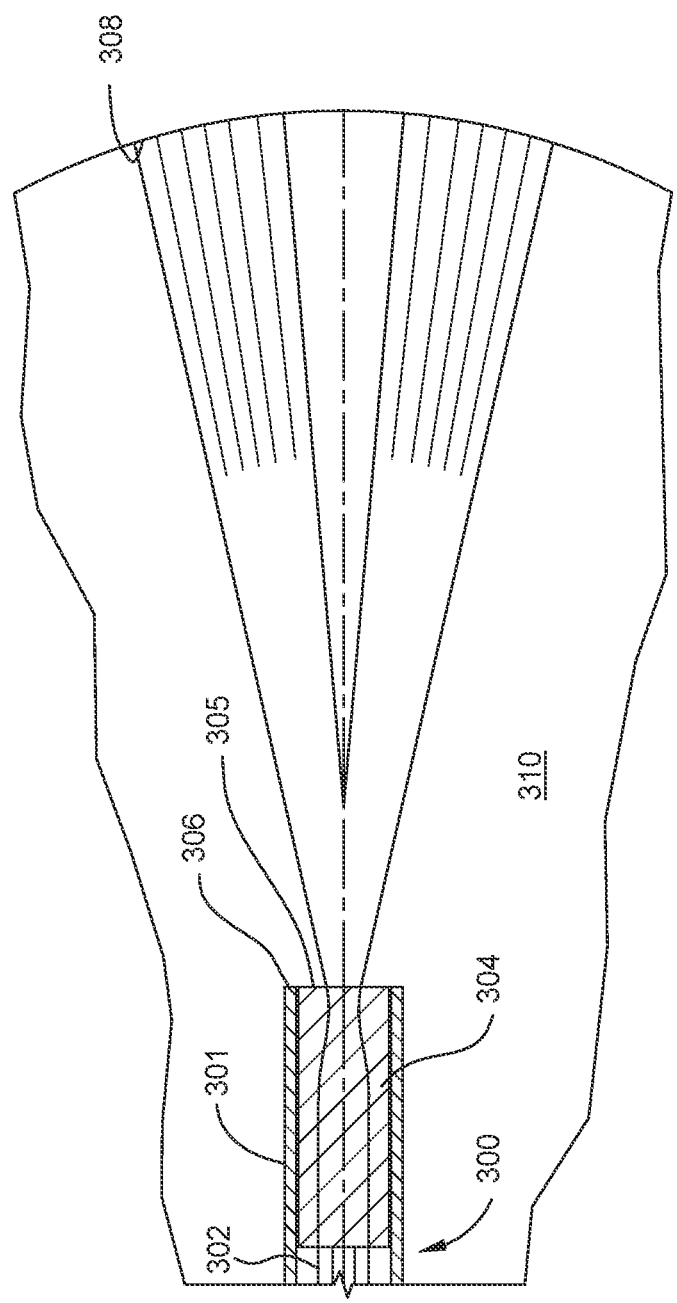
FIG. 3 illustrates aspects of an example multi-spot laser probe in operation.

FIG. 3 illustrates aspects of an example multi-spot laser probe in operation. In this example, distal end 300 of a multi-spot laser probe includes a 2×2 fiber array (which may comprise multiple fibers or a multi-core fiber) optically coupled to lens 304 located at the probe tip 306 within a cannula 301. In this design, lens 304 is the distalmost optical element of probe 300, and the distal surface of lens 304 is in physical contact with eye tissue 310 while probe 300 is inserted in an eye during a procedure. Other embodiments may include additional elements or features. In operation, laser light is transmitted through fiber array 302, refracted by lens 304, and projected onto a retina as a plurality of laser spots 308.

In some surgical cases, blood or another contaminant may build up at or near probe tip 306, causing an occlusion. For example, blood can occlude at the distal surface 305 of lens 304 during a surgical procedure. Blood occluded at distal surface 305 may char and absorb energy from a laser, causing the temperature of lens 304 to rise, potentially causing the lens 304 to melt, adhesives to fail, or injury to the patient. In other instances, blood or another foreign element or contaminant may seep into the space between the outer surface of lens 304 and the inner surface of cannula 301. As in the prior example, such substances may absorb the laser energy, causing the temperature of lens 304 to rise and potentially lead to the issues previously described.

In some cases, an optical element may be located distal to the lens 304. The optical element may be designed to isolate and protect lens 304 (and other components in the probe) from exposure to foreign substances (e.g., tissue or blood in a surgical environment), overheating, and melting. The optical element may comprise one or more elements made of an optically clear material with a high melting and high softening temperature, such as high softening point ceramics or glasses, and may be the distalmost optical element in the distal end 300. In certain examples, the optical element may include sapphire or fused silica.

Figure 4:
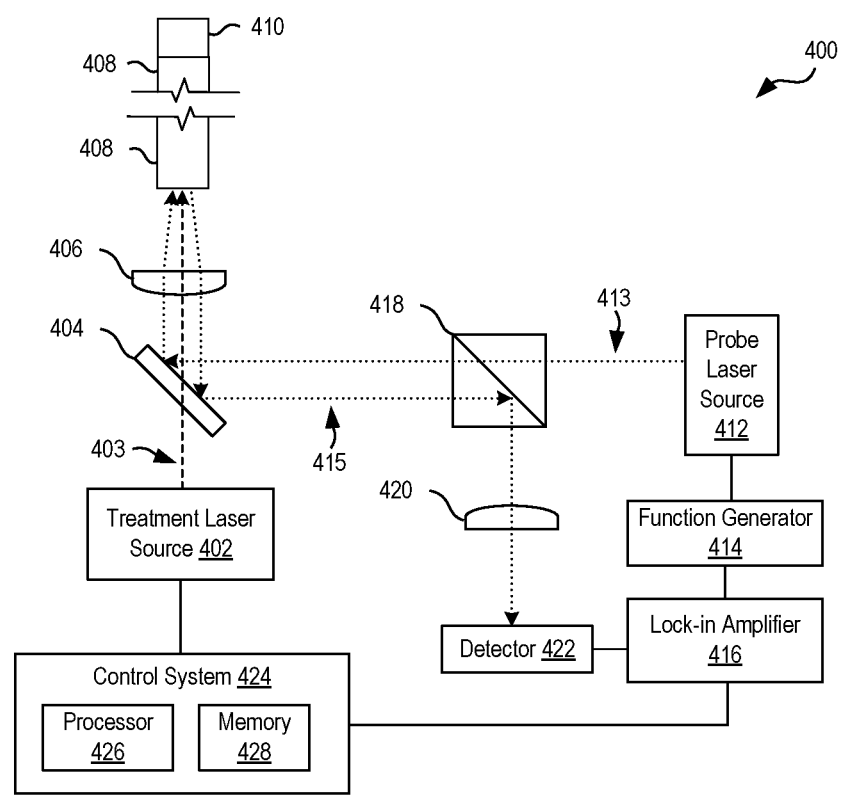
FIG. 4 is a diagram showing an example system for sensing occlusions in a laser probe of an ophthalmic surgical system.

FIG. 4 is a diagram showing an example system 400 for sensing occlusions in a laser probe of an ophthalmic surgical system. In some embodiments, the example system 400 may be included in a laser system of an ophthalmic surgical system such as the laser system 110 of ophthalmic surgical system 100 of FIG. 1. The example system 400 may be used, in some cases, to sense occlusions in laser probes, such as multi-spot laser probes, used to perform laser photocoagulation therapy. The example system 400 may also be used to sense occlusions in other types of optical systems as well, which might or might not relate to ophthalmic surgical procedures. The system 400 may include additional, fewer, or different components than those shown in FIG. 4. Further, the components of system 400 may be arranged in another manner. For example, the treatment laser source 402 and probe laser source 412 may be within the same source and may be on the same axis as one another.

The example system 400 includes a treatment laser source 402 that generates optical signals for use in surgical procedures. For example, the treatment laser source 402 may generate signals used in laser photocoagulation therapy techniques. In some cases, the treatment laser source 402 may include an intercavity-doubled ND:TVO4 (Neodymium Vanadate) continuous wave laser (having a wavelength of approximately 532 nm) or an Argon Ion laser (having a wavelength of approximately 515 nm). In other cases, the treatment laser source may include a femtosecond laser oscillator, such as a Ytterbium-based (e.g., a Yb:Glass or Yb-doped fiber) laser, an Erbium-based (e.g., an Er-doped fiber) laser, a Titanium Sapphire (TiAl2O3) laser, Chromium-based (e.g., Cr:LiSAF Cr:LiCAF, or Cr:LiSGAF) laser, an Alexandrite laser, a neodymium-doped yttrium aluminum garnet (Nd:YAG) laser, a semiconductor- or dye-based laser, or another type of laser for use in the surgical procedure. The treatment laser source 402 may produce relatively high-power optical signals. For example, the treatment laser source 402 may produce optical signals with a power between approximately 30 mW to 3 W. In some embodiments, the treatment laser source 402 generates optical signals having a wavelength between 500 nm and 700 nm (e.g., approximately 532 nm, 577 nm, or 659 nm).

The example system 400 also includes a probe laser source 412 that generates optical signals used to detect the presence of occlusions in the system 400. In some cases, the probe laser source 412 may include a semiconductor (diode) laser. The probe laser source 412 may generate optical signals that are generally low-power, especially when compared with the optical signals generated by the treatment laser source 402. For example, the probe laser source 412 may produce optical signals with a power between approximately 100 uW to 5 mW. The wavelength of the signals generated by the probe laser source 402 may be different from those of the treatment laser source 402, and may be determined, in some cases, by the type of contaminant to be detected by the system 400. For instance, the wavelength of the optical signals generated by the probe laser source 412 may be of a wavelength outside of the absorption spectrum of the contaminant at issue. As an example, in embodiments for detecting blood occlusions, the probe laser source 412 generates optical signals having a wavelength in the range of approximately 600-700 nm (e.g., 635 nm or 650 nm) or in the range of approximately 800-900 nm (e.g., 850 nm), since both wavelength ranges are outside of the absorption spectrum of blood. In some cases, the probe laser source 412 may be the same as the source of the "aiming beam" in an ophthalmic surgical system. That is, the aiming beam may serve a dual purpose of being used by a surgeon to guide the surgical procedure (where the aiming beam shows where the treatment beam is to be applied), and also to detect blood occlusions (since such aiming beams may be between approximately 620-650 nm and therefore, outside of the absorption spectrum of blood).

The example system 400 further includes a number of optical elements for directing the optical signals generated by the treatment laser source 402 and the probe laser source 412. For instance, in the example shown, the system 400 includes a dichroic mirror 404 and a lens 406, optical fiber 408, terminating optical element 410, beamsplitter 418, and lens 420. The system 400 may include additional, fewer, or other optical elements than those shown in FIG. 4. The dichroic mirror 404 is configured to transmit optical signals of a certain wavelength and reflect optical signals of a different wavelength. In the example shown, the dichroic mirror 404 is configured to transmit optical signals from the treatment laser source 402 (as shown in beam path 403) and reflect optical signals from the probe laser source 412 (as shown by beam paths 413, 415). The beamsplitter 418 is configured to transmit a portion of incident optical signals and reflect the remaining portion of optical signals. For instance, the beamsplitter 418 is configured to transmit a portion of the optical signals from the probe laser source 412 (as shown in beam path 413) and reflect another portion of those signals upward (not shown in FIG. 4 for the sake of clarity).

In operation, optical signals from the treatment laser source 402 are directed along the beam path 403 toward the optical fiber 408 and optical signals from the probe laser source 412 are directed along the beam path 413 toward the optical fiber 408. The optical fiber 408 directs the respective optical signals from the laser sources 402, 412 toward the terminating optical element 410. In some embodiments, terminating optical element 410 and at least a portion of the optical fiber 408 are located in a surgical laser probe (e.g., the probe 106 of FIG. 1 or the probe 200 of FIG. 2). For example, the terminating optical element may be a GRIN lens or other type of optical element at a distal end of a laser probe tip. The lens 406 (or other optical elements) may be used to focus the optical signals into the optical fiber 408.

When blood or another type of contaminant is located on the terminating optical element 410, the optical signals from the probe laser source 412 may be reflected back along the beam path 415 toward the detector 422 (reflected by the beamsplitter 418 and focused by the lens 420 as shown). The detector 422 may include a photodetector that receives the reflected optical signals and generates electrical signals based on the received optical signals. The detector 422 may then provide those electrical signals to the control system 424 (indirectly as shown, or directly in some embodiments), which analyzes the signals to detect whether an occlusion is present. If an occlusion is detected, then the control system 424 may disable the treatment laser source 402 before any overheating may occur.

In the example shown, a function generator 414 is communicably coupled to the probe laser source 412. The function generator 414 generates modulation signals that are provided to the probe laser source 412 and operate to modulate the optical signals generated by the probe laser source 412. By modulating the optical signals generated by the probe laser source 412, the optical signals reflected from the terminating optical element may be differentiated from other optical signals that may be received at the detector 422. The system 400 also includes a lock-in amplifier 416 that is communicably coupled to the detector 422 and the function generator 414. The lock-in amplifier 416 may be configured to extract, using the known modulation signal from the function generator 414, electrical signals from the detector 422 that are based on the reflected optical signals from the probe laser source 412. The extracted signals may be referred to as "reflected signals" and may be provided to the control system 424. For example, the lock-in amplifier 416 may filter the reflected signals from the signals provided by the detector 422 based on the modulation signal.

The control system 424 may then make a determination as to whether to disable the treatment laser source 402 based on the signals provided by the lock-in amplifier 416. The determination may be made by any suitable means based on the beam strength of the reflected optical signals from the probe laser source 412. For example, in some implementations, the determination may be made based on a threshold value, wherein a magnitude of the reflected signals is compared with a threshold value. If the magnitude is above the threshold value, then the control system 424 may disable the treatment laser source 402. Otherwise, if the magnitude of the reflected signals is below the threshold value, the control system 424 may continue operation of the treatment laser source 402. In other implementations, the control system 424 may make its determination based on additional or other factors.

The example control system 424 includes a processor 426 and memory 428. The example processor 426 executes instructions, for example, to generate output data based on data inputs. The instructions can include programs, codes, scripts, or other types of data stored in memory. Additionally, or alternatively, the instructions can be encoded as pre-programmed or re-programmable logic circuits, logic gates, or other types of hardware or firmware components. The processor 426 may be or include a general-purpose microprocessor, as a specialized co-processor or another type of data processing apparatus. In some cases, the processor 426 may be configured to execute or interpret software, scripts, programs, functions, executables, or other instructions stored in the memory 428 to perform one or more functions or operations as described herein (e.g., those shown in FIG. 5 and described below). In some instances, the processor 426 includes multiple processors.

The example memory 428 includes one or more computer-readable media. For example, the memory 428 may include a volatile memory device, a non-volatile memory device, or a combination thereof. The memory 428 can include one or more read-only memory devices, random-access memory devices, buffer memory devices, or a combination of these and other types of memory devices. The memory 428 may store instructions that are executable by the processor 426.

In some instances, the control system 424 may be implemented in another manner. For instance, the control system 424 may be implemented as an FPGA (field programmable gate array) or an ASIC (application specific integrated circuit).

Figure 5:
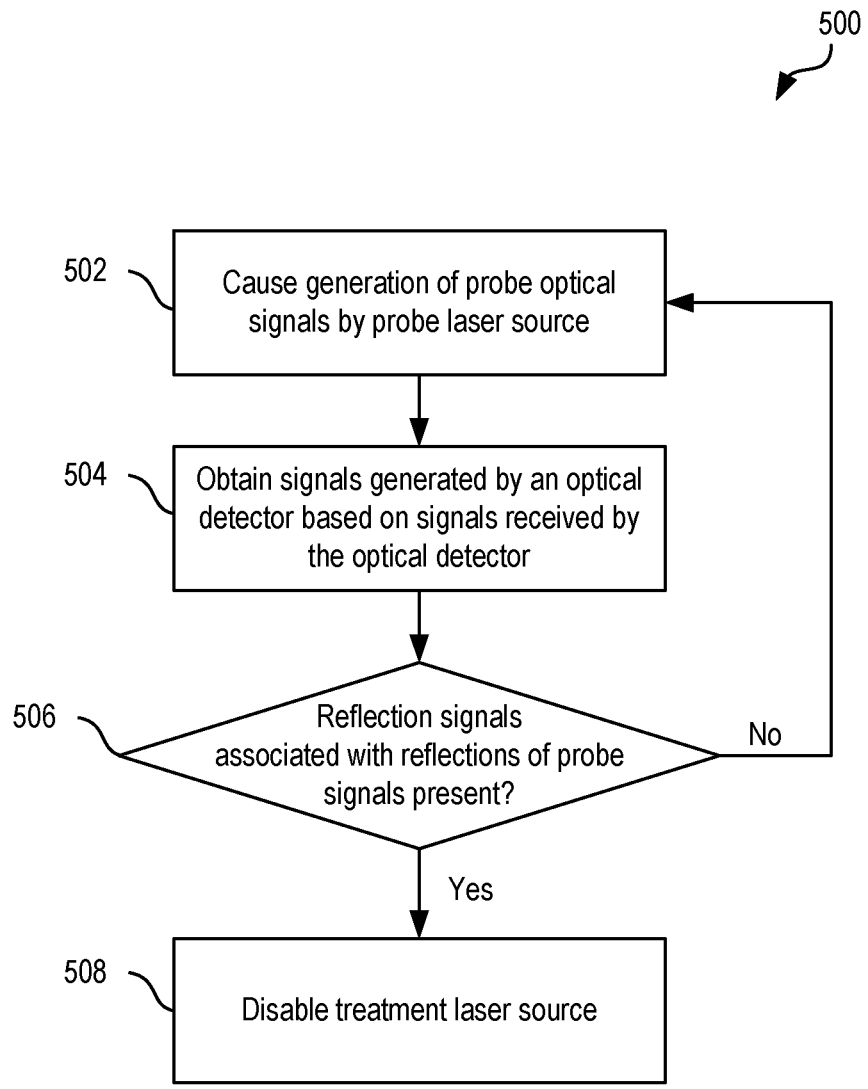
FIG. 5 is a flow diagram of an example process for sensing occlusions in an optical system, such as in a laser probe of an ophthalmic surgical system.

FIG. 5 is a flow diagram of an example process for sensing occlusions in an optical system, such as in a laser probe of an ophthalmic surgical system. Operations in the example process 500 may be performed by components of an ophthalmic surgical system (e.g., the ophthalmic surgical system 100 of FIG. 1 or the system 400 of FIG. 4). For ease of explanation, certain operations in the process 500 are discussed below with respect to terminology of components of the system 400 of FIG. 4. However, it will be understood that the operations of process 500 may be performed by another type of apparatus that includes a data processing apparatus or logic.

At 502, a control system (e.g., control system 424) causes, directly or indirectly, generation of probe optical signals by a probe laser source (e.g., probe laser source 412). The probe laser source may be configured to generate optical signals that are outside of the absorption spectrum of a contaminant to be sensed. For instance, where blood occlusions are to be detected, the probe optical signals may have a wavelength between 600-700 nm or between 800-900 nm. In some embodiments, the probe optical signals may be modulated based on a modulation signal generated by a function generator (e.g., function generator 414). The modulation signal may be used, as described below, to differentiate signals caused by reflections of the probe optical signals and signals caused by other optical signals received at a detector. In some cases, the function generator may directly cause generation of the probe optical signals by driving a laser diode of the probe laser source.

At 504, the control system receives signals generated by an optical detector. In some cases, the optical detector includes a photodetector and the signals received at 504 may be electrical signals generated by the photodetector based on optical signals received by the photodetector.

At 506, the control system determines whether reflection signals associated with reflections of the probe optical signals are present in the signals received at 504. In some cases, detection of the reflection signals may be based on the modulation signal used to modulate the probe optical signals. For instance, a lock-in amplifier (e.g., lock-in amplifier 416) may be used to extract or filter reflection signals caused by the reflected probe optical signals from the signals received from the optical detector at 504. The control system may determine whether reflection signals are present at 506 based on a threshold value, as described above, or in another manner.

If the control system determines that reflection signals are determined to be present at 506, then at 508, the control system disables a treatment laser source (e.g., treatment laser source 402). This may include sending a "kill" signal to the treatment laser source, disabling power to the treatment laser source, physically blocking transmission of optical signals from the treatment laser source (e.g., using a shutter), or disabling the treatment laser source in another manner. In some embodiments, an alert, such as an audible alert, may also be generated in response to detection of the reflection signals at 506. If no reflection signals are determined to be present at 506, then the process 500 may be repeated.

The example process 500 may include additional or different operations, and the operations may be performed in the order shown or in another order. In some cases, one or more of the operations shown in FIG. 5 are implemented as processes that include multiple operations, sub-processes, or other types of routines. In some cases, operations can be combined, performed in another order, performed in parallel, iterated, or otherwise repeated or performed another manner.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer-readable storage medium for execution by, or to control the operation of, data-processing apparatus. A computer-readable storage medium can be, or can be included in, a computer-readable storage device, a computer-readable storage substrate, a random or serial access memory array or device, or a combination of one or more of them. Moreover, while a computer-readable storage medium is not a propagated signal, a computer-readable storage medium can be a source or destination of computer program instructions encoded in an artificially generated propagated signal. The computer-readable storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The computer system may include one or more data processing apparatuses coupled to computer-readable media storing one or more computer programs that may be executed by the one or more data processing apparatuses, and one or more interfaces for communicating with other computer systems.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Embodiments of the present disclosure provide systems and methods for sensing occlusions in optical systems, such as in laser probes of an ophthalmic surgical system, that may overcome limitations of conventional systems and methods. It will be appreciated that above-disclosed and other features and functions, or alternatives thereof, may be desirably combined into many other different systems or applications in accordance with the disclosure. It will also be appreciated that various presently unforeseen or unanticipated alternatives, modifications, variations, or improvements therein may be subsequently made by those skilled in the art which alternatives, variations and improvements are also intended to be encompassed by the following claims.

What is claimed is:

1. An ophthalmic surgical system for detecting occlusions in a surgical probe, comprising:
   a connector configured to couple to the surgical probe comprising one or more optical elements;
   a treatment laser source;
   a probe laser source;
   a function generator communicably coupled to the probe laser source, the function generator configured to generate a modulation signal to modulate a probe optical signal generated by the probe laser source;
   a detector;
   a set of optical elements configured to:
      receive a treatment optical signal from the treatment laser source and direct the treatment optical signal along a first beam path toward the one or more optical elements of the surgical probe;
      receive a modulated probe optical signal from the probe laser source and direct the modulated probe optical signal along a second beam path toward the one or more optical elements of the surgical probe; and
      receive a reflection of the modulated probe optical signal caused by one or more of the optical elements in the surgical probe and direct the reflection of the modulated probe optical signal toward the detector; and
   a control system comprising a processor and memory storing executable instructions, the control system communicably coupled to the detector;
   a lock-in amplifier communicably coupled to the detector, the function generator, and the control system, the lock-in amplifier configured to extract, based on the modulation signal, electrical signals from the detector that are based on the reflected modulated probe optical signal, wherein the lock-in amplifier is further configured to provide the extracted electrical signals to the control system; and
   wherein the control system executable instructions, when executed by the processor, causes the control system to:
      determine a presence or an absence of an occlusion in the surgical probe based on the extracted electrical signals; and
      disable the treatment laser source based on the determined presence of the occlusion.

2. The system of claim 1, wherein the set of optical elements comprises a beam splitter arranged to transmit the modulated probe optical signal along the second beam path and to reflect the reflection of the modulated probe optical signal toward the detector.

3. The system of claim 1, wherein the set of optical elements comprises a dichroic mirror configured to transmit the treatment optical signal and to reflect the modulated probe optical signal.

4. The system of claim 1, wherein:
the treatment laser source is configured to generate the treatment optical signal having a wavelength between 500-600 nm (nanometers); and
the probe laser source is configured to generate the probe optical signal having a wavelength between 600-700 nm or between 800-900 nm.

5. The system of claim 1, wherein the set of optical elements comprises a terminating optical element, and the detector is arranged to receive reflections of optical signals caused by the terminating optical element.

6. The system of claim 1, wherein the set of optical elements is arranged to direct optical signals generated by the probe laser source toward an optical fiber, and at least one of the optical elements in the set of optical elements is configured to direct optical signals generated by the treatment laser source toward the optical fiber.

7. The system of claim 1, wherein the probe laser source is configured to generate optical signals having a wavelength different from that of the treatment laser source.

8. The system of claim 1, wherein the control system executable instructions, when executed by the processor, further enable the control system to:
determine a beam strength of the reflected modulated probe optical signal based on the extracted electrical signals.

9. The system of claim 8, wherein the determined presence or absence of the occlusion is based on the determined beam strength of the reflected modulated probe optical signal.

10. The system of claim 9, wherein the control system disables the treatment laser source based on a determination that the determined beam strength of the reflected modulated probe optical signal is above a threshold value indicating the presence of the occlusion.

* * * * *